United States Patent
Roulier et al.

(10) Patent No.: US 6,180,122 B1
(45) Date of Patent: Jan. 30, 2001

(54) SOLID COSMETIC COMPOSITION AND USES THEREOF

(75) Inventors: Veronique Roulier, Paris; Eric Quemin, Tremblay en France, both of (FR)

(73) Assignee: L'Oreal, Paris (FR)

( * ) Notice: Under 35 U.S.C. 154(b), the term of this patent shall be extended for 0 days.

(21) Appl. No.: 09/215,296

(22) Filed: Dec. 18, 1998

(30) Foreign Application Priority Data

Dec. 19, 1997 (FR) .................................. 97 16173

(51) Int. Cl.$^7$ ....................................... A61K 6/00
(52) U.S. Cl. ............................ 424/401; 424/64; 424/70.7
(58) Field of Search ............................... 426/573

(56) References Cited

U.S. PATENT DOCUMENTS 5,498,436 * 3/1996 Modliszewski et al. ............ 426/573

FOREIGN PATENT DOCUMENTS 0 225 154   6/1987  (EP) .
2 288 186  10/1995  (GB) .

OTHER PUBLICATIONS

Laaman T.R. "The Use of Gellan Gum in Frozen Desserts" Research Disclosure, vol. 348, No. 055, Dec. 1991, XP002080511, Emsworth, GB.

Sanderson G.R. Et Al.: "Gellan Gum in Combination with other Hydrocolloids" 1988, IRL, Oxford GB XP002080512 Gums Stab. Food Ind 4, (Pro. Int. Conf.) , pp. 301–308 *pp. 301–303*.

Database WPI, Section Ch, Week 9713, Derwent Publications Ltd., London, GB; Class A96, AN 97–140815, XP002080513 & JP 09 020649 A (SANEIGAN FFI KK), Jan. 21, 1997,*abrege*.

* cited by examiner

*Primary Examiner*—Shelley A. Dodson
*Assistant Examiner*—Konata M. George
(74) *Attorney, Agent, or Firm*—Oblon, Spivak, McClelland, Maier & Neustadt, P.C.

(57) ABSTRACT

A solid composition free of fillers, comprising an aqueous phase, wherein said aqueous phase comprises a hydrocolloid combination of gellane gum and at least one other hydrocolloid, wherein said gellane gum is present in an amount of at least 2% by weight, relative to the total weight of the composition, and wherein said hydrocolloid combination is present in an amount of less than 20% of the total weight of the composition, formable as tubes, pencils or bars, and useful to care for and/or treat the skin, the scalp, the hair or mucous membranes, to make up the skin and/or keratin fibers such as the eyelashes and the hair, and to style and/or shape keratin fibers, and in particular the hair.

20 Claims, No Drawings

SOLID COSMETIC COMPOSITION AND USES THEREOF

BACKGROUND OF THE INVENTION

1. Field of the Invention

The present invention relates to a solid composition for topical application, as well as to its use in the cosmetic and/or dermatological fields, in particular to care for and/or treat the skin, the scalp, the hair or mucous membranes, to make up the skin and/or keratin fibres such as the eyelashes and the hair, and to style and/or shape keratin fibres, and in particular the hair.

2. Description of the Background

Products in solid form are known in the cosmetics industry. As products of this type, mention may be made, for example, in the field of make-up, of tubes or "sticks" of lipstick, of foundation or of eyeshadow; in the field of skin care or lip care, of lip repair pencils and of depigmenting, make-up-removing or moisturizing tubes or "sticks"; in the field of hygiene, of deodorant sticks and of moussing sticks or bars to shave or wash the skin.

Wax-based stick formulations have certain drawbacks: they have a greasy nature which is not appreciated by users, and they lack freshness when applied. In addition, it is difficult to introduce hydrophilic active agents therein.

Moreover, non-greasy sticks such as deodorant sticks generally contain a relatively large amount of fatty acid salts which can have an irritant nature for applications such as facial care. Moreover, these sticks leave a sticky film when applied to the skin.

In addition, aqueous rigid gels are described in WO-A-97/17055 and WO-A-97/17053. However, these gels require the use of a fairly large concentration of gelling agent or use a specific preparation technique—extrusion. In addition, the sticks described in WO-A-97/17055 lack transparency and, on account of the high concentration of gelling agent, lack freshness and softness when applied to the skin, and those described in WO-A-97/17053 must be moistened at the time of use.

Moreover, EP-A-803,245 describes aqueous solid compositions containing heat-reversible polysaccharides, a wetting agent and a powdery phase (fillers). However, the presence of a powdery phase can entail the following drawbacks: presence of a visible trace after applying the composition to the skin and reduced feeling of comfort. In addition, when the powdery phase is removed from the composition described in EP-A-803,245, a composition which is neither sufficiently solid nor sufficiently stable and which does not transfer onto the skin in a satisfactory manner is obtained.

Thus, there is still a need for a solid composition for topical application which does not have the drawbacks of the prior art.

SUMMARY OF THE INVENTION

The inventors have discovered, unexpectedly, a specific hydrophilic gelling system which makes it possible to prepare homogeneous, rigid aqueous compositions which are stable even at low gelling agent contents and even in the absence of fillers, and which do not necessarily require the use of a specific preparation technique. The compositions obtained can contain a large amount of water and thus have a sensation of freshness when applied while at the same time giving an impression of softness. In addition, they allow product to be applied directly to the skin without the need for prior moistening.

The object of the present invention is a solid composition free of fillers, comprising an aqueous phase, wherein said aqueous phase comprises a hydrocolloid combination of gellan gum and at least one other hydrocolloid, wherein said gellan gum is present in an amount of at least 2% by weight, relative to the total weight of the composition, and wherein said hydrocolloid combination is present in an amount of less than 20% of the total weight of the composition.

DETAILED DESCRIPTION OF THE INVENTION

The term "free of fillers" means that the composition contains no insoluble dyes or pigments or powders. The composition of the invention is, in particular, free of powders such as talc, starch, acrylate polymer and copolymer, mica, kaolin, polyamide (nylon), polyethylene silica and silicone powders.

Moreover, the term "hydrocolloid" means a water-soluble macromolecule which does not modify the water activity value of the composition containing it.

In addition, the term solid composition means any composition with a compression strength of greater than or equal to 20 grams, at room temperature (20–25° C.), after penetration by an axisymmetrical probe with a diameter of 0.8 cm into the matrix of the composition to a depth of 1 mm at a speed of 0.5 mm/s and removal of the said probe from the matrix of the composition at a speed of 0.5 mm/s; the compression strength is measured with an analyzer such as the "LFRA texture analyzer" sold by the company Stevens/Mechtric.

The solid composition obtained can be applied directly to a support, i.e. it does not need to be moistened in order to be applied to the support, and in particular to the skin. The term "support" for the composition according to the invention means any surface on which a topical application may be made, in particular the skin, keratin fibres such as the eyelashes and the hair, the scalp and mucous membranes such as the lips.

In addition, unlike solid compositions containing a high proportion of gelling agents, the composition of the invention has the advantage of not leaving a visible powdery deposit when it is applied to a support. Moreover, it has the property of being transparent or translucent in the absence of oil.

It is known practice in the food sector to use gellane gum, including its use as a mixture with another gum, in order to obtain gelled products. However, the products obtained are gelled but not solid within the sense intended in the present application, i.e., they do not have a compression strength of greater than or equal to 20 grams: they are brittle, so that they can be consumed in portions, and they consequently do not allow a homogeneous film to be deposited on the skin. This is therefore an entirely different type of product.

Moreover, the gellane gum used as sole gelling agent at 2% gives a composition which is, admittedly, solid, but is crumbly and brittle, and is thus unsuitable for cosmetic or dermatological application. In addition, by increasing the amount of gellan gum, an opaque composition is obtained which applies poorly to a support such as the skin. Only the combination claimed makes it possible to obtain a solid composition with good properties of both solidity and transfer.

Thus, the solid composition according to the invention has a good transfer property, i.e., when applied to a support, it releases an effective amount of product onto this support.

In the composition according to the invention, the gellan gum is present in an amount of at least 2% of the total weight of the composition, for example in an amount ranging from 2 to 15%, preferably from 2 to 8% and better still from 2 to 4%, of the total weight of the composition.

The hydrocolloid(s) used in combination with the gellan gum can be chosen, for example, from the group formed by:

cellulose or its derivatives such as carboxymethylcellulose, hydroxypropylcellulose, methylcellulose, hydroxypropylmethylcellulose or hydroxyethylcellulose, as well as celluloses modified in particular by grafting an alkyl group;

algal extracts such as agar-agar, carrageenans and alginates;

seed extracts such as carob gum, guar gum and guar gums modified in particular by grafting an alkyl group;

plant exudates such as gum arabic, karaya gum, gum tragacanth and ghatti gum;

microorganism exudates such as xanthan gum;

fruit extracts such as pectins;

gelling agents of animal origin such as gelatin and caseinates;

water-soluble gelling synthetic polymers such as polyacrylic acids, optionally crosslinked with an alkyl chain, such as the "Carbopol" or "Pemulen" products from the company Goodrich;

silicon derivatives such as synthetic hectorites, for instance the products "Laponite RD and RDS" sold by the company Waverly, and aluminium magnesium silicates such as the product "Veegum" sold by the company Vanderbilt, or a mixture of these compounds.

The hydrocolloid used in the composition according to the invention in combination with the gellan gum is preferably chosen from carob gum, xanthan gum, cellulose derivatives and a modified guar gum, and mixtures of these compounds. It is more particularly xanthan gum, carboxymethylcellulose or a modified guar gum. This modified guar gum may in particular be hydroxypropylguar.

The hydrocolloid(s) combined with the gellane gum is (are) present in the composition according to the invention in an amount which can vary within a wide range. Thus, this amount can range, for example, from 1 to 10%, preferably from I to 5% and, better still, from 2 to 4%, of the total weight of the composition.

Depending on the proportions, and in particular when the total amount of hydrocolloids exceeds 4%, the mixture can advantageously be prepared in a twin-screw extruder according to the technique described in EP-A-667,148.

The aqueous phase of the composition according to the invention represents from 60 to 97%, and preferably from 80 to 95%, of the total weight of the composition.

Advantageously, the solid composition according to the invention is a composition intended for topical application, in particular cosmetic or dermatological application. Such a composition comprises a medium which is physiologically acceptable, in particular for the skin, mucous membranes, the nails, keratin fibres and/or the hair.

According to a particular mode of the invention, the composition also comprises at least one oil, this addition of oil giving a greater feeling of comfort when the composition is applied to the skin.

Among the oils which can be used, mention may be made of mineral oils, oils of plant origin, oils of animal origin, synthetic oils such as fatty esters, silicone oils such as volatile silicone oils, polymethylsiloxanes, polymethylphenylsiloxanes, polysiloxanes modified with fatty acids, fatty alcohols or polyoxyalkylenes, fluorosilicones and perfluoro oils. Other fatty substances can be added, such as fatty acids, fatty alcohols and waxes.

The oil(s) and the other fatty substances which may be present constitute the fatty phase.

The fatty phase can be present in proportions ranging, for example, up to 30%, preferably from 0.1 to 20% and, better still, from 0.5 to 10%, of the total weight of the composition, these proportions varying depending on the chosen application.

The oil can be introduced into the aqueous phase in the presence of one or more surfactants to ensure better dispersion.

The compositions according to the invention can thus also contain one or more nonionic, anionic, cationic or amphoteric surfactants usually used in the cosmetics and/or dermatological fields. When it is present, the amount of surfactant preferably ranges from 0.05 to 8%, and, better still, from 0.05 to 5%, of the total weight of the composition.

It is possible to modify the rigidity of the compositions according to the invention by adding thereto one or more salts which will increase this rigidity. These salts can be chosen from the salts of monovalent, divalent or trivalent metals, and more particularly alkali metal and alkaline-earth metal salts and in particular sodium and calcium salts. The ions constituting these salts can be chosen, for example, from carbonates, bicarbonates, sulphates, glycerophosphates, borates, chlorides, nitrates, acetates, hydroxides and persulphates, as well as the salts of α-hydroxy acids (citrates, tartrates, lactates, malates) or of fruit acids, or alternatively amino acid salts (aspartate, arginate, glycolate, fumarate). The amount of salt can range from 0.01 to 2%, and preferably from 0.1 to 1%, of the total weight of the composition.

Preferably, the salt is chosen from calcium, magnesium or strontium nitrate, calcium or magnesium borate, calcium, sodium, magnesium, strontium, neodymium or manganese chloride, magnesium or calcium sulphate and calcium or magnesium acetate, and mixtures thereof.

The compositions according to the invention can contain additives usually used in the cosmetics and/or dermatological fields. Mention may be made in particular of antioxidants or anti-free-radical agents, water-soluble dyes such as FD&C Red No. 4 and D&C Green No. 5, or alternatively liposoluble dyes if the composition contains a fatty phase, solvents, hydrophilic or lipophilic active agents, and fragrances.

The active agents can be chosen, for example, from moisturizers or wetting agents such as polyols and in particular glycerol, UV screening agents, antidandruff agents, conditioners, deodorant active agents, depigmenting or bleaching agents, tensioning agents, anti-wrinkle agents, latices and pseudo-latices, and any other active agent which is appropriate for the end use of the solid product considered.

As solvents, mention may be made of primary alcohols such as ethanol and isopropanol, glycols such as propylene glycol, butylene glycol, dipropylene glycol and diethylene glycol, and glycol ethers such as the Cl-$C_4$ alkyl ethers of mono-, di- or tripropylene glycol or of mono-, di- or triethylene glycol, and mixtures thereof.

As latices and pseudo latices, mention may be made, for example, of dispersions of synthetic polymers of polycondensate type or of radical type. As polymers constituting the latex or the pseudolatex, mention may be made of anionic, cationic, nonionic or amphoteric polyurethanes, acrylic polyurethanes, polyurethane-polyvinylpyrrolidones, polyester-polyurethanes, polyether-polyurethanes, polyureas, acrylic polymers, acrylic copolymers, sulphonated isophthalic acid polymers, as well as polymers resulting from the radical polymerization of one or more radical monomers. As synthetic polymer which is appropriate for use as a latex, mention may be made in particular of the dispersions of polyester-polyurethane and of polyether-polyurethane, sold under the names "Sancure 2060" (polyester-polyurethane), "Sancure 2255" (polyester-polyurethane), "Sancure 815" (polyester-polyurethane), "Sancure 878" (polyether-polyurethane) and "Sancure 861" (polyether-polyurethane) by the company Sanncor, under the names "Neorez R974" (polyester-polyurethane), "Neorez R981 " (polyester-polyurethane) and "Neorez R970" (polyether-polyurethane) by the company ICI, and the acrylic copolymer dispersion sold under the name "Neocryl XK-90" by the company Zeneca.

These additives can be present in the final composition in an amount of from 0 to 50%, preferably from 0.5 to 20%, and even more particularly between 0.5 and 10%, of the total weight of the composition.

Needless to say, a person skilled in the art will take care to select this or these optional additives and/or the amounts thereof such that the advantageous properties intrinsically associated with the composition in accordance with the invention are not, or are not substantially, adversely affected by the addition(s) envisaged.

The compositions according to the invention can constitute care and/or conditioning and/or hygiene products for the skin, mucous membranes, the scalp and/or the hair. Among the care, conditioning or hygiene products in the form of a bar, a stick or a pencil, mention may be made, for example, in hair care, of solid gels for styling and/or shaping the hair; in skin care, of moisturizing products, slimming products, depigmenting and bleaching products and of products for lip care; for facial and/or body hygiene, of shaving products and deodorants.

Another object of the invention consists of a cosmetic treatment process for the care and/or conditioning and/or hygiene of the skin, the hair, the scalp and/or mucous membranes, this process comprises applying a solid composition as defined above to the skin, the hair, the scalp and/or mucous membranes.

The compositions according to the invention can also constitute make-up products, such as lipsticks, foundations, eyeshadows, blushers, concealers, mascaras, lip pencils, eye pencils and sticks for colouring locks of hair. They can in particular constitute "transfer-resistant" make-up products, i.e., products which deposit a film which does not transfer or migrate or stain the support with which the make-up product applied to the skin may be placed in contact (clothing, glass, cup, etc.).

Thus, the object of the present invention is the use of the composition according to the invention to obtain a transfer-resistant make-up product. When the make-up product also contains a latex, a product with good staying power is obtained.

The object of the present invention is also a process for making up the skin and/or keratin fibres, which comprises applying a solid composition as defined above to the face, the lips, the area around the eyes, the cheeks, the contour of the lips, the eyelashes, the eyebrows, the hair and/or the eyelids.

The examples which follow serve to illustrate the invention without, however, limiting its scope. The percentages are expressed on a weight basis except where otherwise mentioned.

| Example 1: Moisturizing stick | |
|---|---|
| Gellan gum | 2% |
| Xanthan gum | 1% |
| Water | qs 100% |

The stick is prepared by mixing the constituents at 80° C. with stirring and casting while hot.

The stick obtained is transparent and deposits a fresh film when applied to the skin.

| Example 2: Lipstick | |
|---|---|
| Gellan gum | 2% |
| Xanthan gum | 1% |
| FD&C Red No. 4 | 0.3% |
| Water | qs 100% |

This lipstick is prepared according to the same procedure as in Example 1.

| Example 3: Moisturizing stick | |
|---|---|
| Gellan gum | 2.75% |
| Hydroxypropylguar (HP60 sold by the company Rhône-Poulenc) | 2.75% |
| Glycerol | 5% |
| Water | qs 100% |

This stick is prepared according to the process described in EP-A-667,146, in a twin-screw extruder-cooker (such as "BC 21" from the company Clextral), whose structure is as follows:

| | Inlet → | | | | | | | | → Outlet | | |
|---|---|---|---|---|---|---|---|---|---|---|---|
| Screw structure | DF | DF | BL | DF | BL | BL | CF | DF | DF | DF | DF |
| Length of the jaws (mm) | 100 | 50 | 50 | 50 | 50 | 50 | 50 | 25 | 50 | 100 | 25 |
| Length of the screw pitch (mm) | 33 | 25 | | 16.6 | | 16.6 | | −16.6 | 16.6 | 16.6 | 16.6 |

"DF" corresponds to a helical screw threading, in which the pitch conveys the treated material from the mixer inlet to the outlet; "CF" corresponds to a helical screw threading of opposite pitch to that of the previous one (denoted with a negative pitch length value) which pushes the treated material in the direction from the mixer outlet to the inlet, such threading including longitudinal grooves to ensure passage of the material to the mixer outlet; "BL" corresponds to a two-lobed section which includes, along its entire length, a succession of lobes offset by 90° relative to each other.

Conditions of the extrusion:
Extruder temperature: 100° C.
Speed: 500 rpm
Flow rate: 3 kg/h

| Example 4: Foundation | |
|---|---|
| Gellan gum | 3% |
| Carboxymethylcellulose | 1% |
| FD&C Red No. 4 | 0.2% |
| D&C Green No. 5 | 0.1% |
| Plant oil | 5% |
| Water | qs 100% |

This foundation is prepared according to the process of Example 1.

The disclosure of french patent application 9716173, filed Dec. 19, 1997, is hereby incorporated by reference.

What is claimed is:

1. A solid composition free of fillers, comprising an aqueous phase, wherein said aqueous phase comprises a hydrocolloid combination of gellan gum and at least one other hydrocolloid, wherein said gellan gum is present in an amount of at least 2% by weight, relative to the total weight of the composition, and wherein said hydrocolloid combination is present in an amount of less than 20% by weight of the composition, said composition having a compressive strength>20 grams at room temperature.

2. Composition according to claim 1, wherein said at least one other hydrocolloid is selected from the group consisting of
   cellulose and its derivatives;
   algal extracts;
   seed extracts;
   plant exudates;
   microorganism exudates;
   fruit extracts;
   gelling agents of animal origin;
   water-soluble gelling synthetic polymers;
   silicon derivatives;
   and mixtures thereof.

3. Composition according to claim 1, wherein said at least one other hydrocolloid is selected from the group consisting of xanthan gum, cellulose derivatives, carob gum and a modified guar gum, and mixtures thereof.

4. Composition according to claim 1, wherein the gellan gum is present in an amount ranging from 2 to 15%, of the total weight of the composition.

5. Composition according to claim 4, wherein the gellan gum is present in an amount ranging from 2 to 8%, of the total weight of the composition.

6. Composition according to claim 1, wherein said at least one other hydrocolloid is present in an amount ranging from 1 to 10%, of the total weight of the composition.

7. Composition according to claim 6, wherein said at least one other hydrocolloid is present in an amount ranging from 1 to 5%, of the total weight of the composition.

8. Composition according to claim 1, wherein the aqueous phase is present in an amount of from 60 to 97% of the total weight of the composition.

9. Composition according to claim 1, which additionally comprises at least one fatty phase.

10. Composition according to claim 9, wherein the fatty phase is present in an amount ranging up to 30%, of the total weight of the composition.

11. Composition according to claim 10, wherein the fatty phase is present in an amount of from 0.1 to 20%, of the total weight of the composition.

12. Composition according to claim 1, which additionally comprises at least one surfactant.

13. Composition according to claim 1, which additionally comprises at least one salt.

14. Composition according to claim 1, which additionally comprises at least one cosmetic or dermatological ingredient.

15. Composition according to claim 1, which additionally comprises at least one additive selected from the group consisting of antioxidants, anti-free-radical agents, water-soluble or liposoluble dyes, solvents, lipophilic or hydrophilic active agents and fragrances.

16. Composition according to claim 1, which additionally comprises at least one active agent selected from the group consisting of moisturizers, UV screening agents, antidandruff agents, conditioners, deodorants, depigmenting agents, bleaching agents, tensioning agents, anti-wrinkle agents, latices and pseudolatices.

17. Composition according to claim 1, in the shape of a stick, pencil or bar.

18. Make-up product comprising the composition according to claim 1.

19. Process for making up the skin and/or keratin fibres, which comprises applying the solid composition according to claim 14 to the face, lips, area around the eyes, cheeks, contour of the lips, eyelashes, eyebrows, hair and/or eyelids.

20. Process for cosmetic care and/or conditioning and/or hygiene of the skin, hair, scalp and/or mucous membranes, which comprises applying a solid composition according to claim 14 to the skin, the hair, the scalp and/or mucous membranes.

* * * * *